United States Patent [19]
Reintjes et al.

[11] Patent Number: 5,572,320
[45] Date of Patent: Nov. 5, 1996

[54] FLUID SAMPLER UTILIZING OPTICAL NEAR-FIELD IMAGING

[75] Inventors: John F. Reintjes, Alexandria, Va.; Paul L. Howard, Westchester, Pa.

[73] Assignee: The United States of America as represented by the Secretary of the Navy, Washington, D.C.

[21] Appl. No.: 342,053

[22] Filed: Nov. 17, 1994

[51] Int. Cl.$^6$ .................................................. E01N 15/02
[52] U.S. Cl. ......................... 356/335; 356/336; 356/246; 356/70
[58] Field of Search .............................. 356/70, 335, 336, 356/338, 361, 246; 73/53.05, 53.01, 61.48, 64.56, 863.83

[56] References Cited

FOREIGN PATENT DOCUMENTS 0507746 10/1992 European Pat. Off. .
0545274 2/1993 Japan .

*Primary Examiner*—Richard A. Rosenberger
*Assistant Examiner*—Robert Kim
*Attorney, Agent, or Firm*—Thomas E. McDonnell; Edward F. Miles

[57] ABSTRACT

An optical scheme for in situ identification of particulates in fluid such as engine oil, in which a portion of the fluid flow is tapped, fed via a conduit to a pair of optically transparent opposed plates, imaged through the plates, and the fluid returned to the main flow. Imaging is preferably done with a laser and photodetector array, and the output fed to a computer for image processing. Separation between the plates ensures that all the oil therebetween will be in the imaging system's near field.

Preferably, the computer counts the number of particles in the oil, and classifies their shape, by scanning the image until it hits an object (i.e. hits an opaque pixel), using known chain code to trace the object's outline, determining the object's aspect ratio, and repeating for each object in the image.

One embodiment uses a planar rotary member which is scalloped about its periphery. The scallops act to push oil continuously against an outer casing. The casing has a light source for directing coherent light at the rotary member, which is made reflective. As the rotary member moves in the casing, it carries fluid with it, and packs the fluid against the casing. The gap between the light source and the rotary member then constitutes the passageway which is imaged.

4 Claims, 3 Drawing Sheets

FLUID SAMPLER UTILIZING OPTICAL NEAR-FIELD IMAGING

BACKGROUND OF THE INVENTION

Determination of the quantity, size, characteristics, and types of particulate matter in fluids is important for many applications such as monitoring fluids in engines and rotating machinery, industrial quality control, food processing, medical analysis, and environmental control. For example, as an engine ages, it flakes metal particulates into its lubricating oil. It is known that the size, number, and shape of particulates correspond to engine condition, and can alert one to imminent engine failure. Predicting failure is critically important in aircraft engines, where sudden failure could result in a crash and loss of life. Heretofore, oil particulates were checked by extracting an oil sample while the aircraft is on the ground, and sending the oil to a laboratory for testing. Although necessary for safety, this process is time consuming.

In the early stages of wear engines shed smaller particulates, on the order of 50 microns or less, and that these particulates have characteristic shapes indicative of the type, source, and nature of the wear. As the wear process progresses, the amount and size of particles increase. Sensing and identifying smaller particles allows early identification of faults, more time for corrective maintenance action, and fewer unexpected catastrophic failures. Current methods to accomplish this are costly, time consuming, use only a small sample of oil, and are not thorough in fault identification. Any system which can monitor particulates automatically in situ would increase engine life and availability. Similarly, blood cells are of the order of 20 microns or less, and such a system could also perform similarly automated blood counts.

Copending U.S. patent application 08/143,370 (attorney docket no. 74,852) by Reintjes et al. discloses a system which optically images a fluid flow, detects the image, and classifies the size and shape of particulates in the fluid. However, that system images an entire fluid line, such as an oil line in an engine. To do this effectively, without missing many particulates, the imaging system must have a large depth of view, which severely restricts the magnification by the optics between the pipe and the detector. With such a small magnification, that system cannot resolve extremely small particulates, for example 50 microns or smaller.

SUMMARY OF THE INVENTION

Accordingly, an object of the invention is to permit monitoring of particulates in a fluid, in which the particulates are on the order of 50 microns or less.

Another object is to do so in situ and continuously, without requiring downtime of any system dependent on the fluid.

Another object is to do so by optically imaging a portion of the fluid.

In accordance with these and other objects made apparent hereinafter, the invention concerns an imaging system, and method of imaging, which employ a fluid passageway and a light source disposed so as to direct spatially coherent light transverse to the direction of flow in the passageway. The passageway is of a material which permits the light to pass through, and is of a width which causes the diffraction pattern of light exiting the passageway to be characteristic of the optical near field, rather than the far field.

Because the passageway is sufficiently thin that the diffraction pattern of light exiting it is characteristic of the optical near field, the passageway will be very thin in most, if not all, practical applications, and have a corresponding small depth of view. This permits use of imaging optics having a much higher magnification than is possible with the invention of U.S. patent application 08/143,370, with a corresponding ability to image particulates as small as 10 microns or smaller.

Moreover, because the system images only the passageway's near field, the system will image all opaque matter in the passageway clearly regardless of whether the opaque material is near the system's focal plane. When combined with imaging optics and a detector, this permits one to image, and detect, all opaque particulates in a fluid traveling through the passageway, not just those particulates in the vicinity of the optical focal plane, permitting an increase in the counting efficiency and statistical accuracy of the system.

When further combined with an computer or other automatic processing circuit (e.g. a neural network), the system can process images continuously, quickly, and automatically in situ. This permits monitoring of particulates in a fluid flowing through the passageway in real time. If, for example, the fluid is engine oil, one can monitor number, shape, and size of particulates in the oil continuously, without needing to shut down the engine. This in turn permits early detection of engine failure, while simultaneously eliminating engine downtime which heretofore was needed to send samples of engine oil to a laboratory for examination.

Thus by identifying small particles by size and shape, and by continuously sampling the oil, the present invention can, provide a more thorough analysis of wear and thereby introduce a quantum improvement in diagnostic capability. The present invention provides useful information by continuously sampling the engine oil and can provide a histogram indicating the distribution of particulate sizes, shapes, etc.

These and other objects, features, and advantages of the invention are further understood from the following detailed description of particular embodiments. It is understood, however, that the invention is capable of application beyond the precise details of these embodiments. Changes and modifications can be made to the embodiments that do not affect the spirit of the invention, nor exceed its scope, as expressed in the appended claims. The embodiments are described with particular reference to the accompanying drawings, wherein:

BRIEF DESCRIPTION OF THE DRAWINGS

FIG. 4 is a sectional view in the direction of lines 4—4 of FIG. 5; FIG. 5 is a sectional view in the direction of lines 5—5 of FIG. 4.

DETAILED DESCRIPTION

Figure 1:
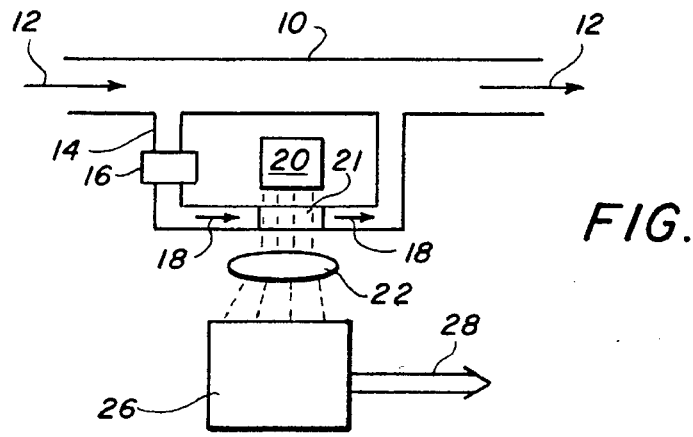
FIG. 1 is a schematic illustrating the basic elements of an embodiment of the invention.

With reference to the drawing figures, wherein like numbers indicate like parts throughout the several views, FIG. 1 shows a pipe 10 which carries a fluid such as engine oil. A portion of the flow is tapped off continuously through line 14, aided as necessary by booster pump 16. Tapped fluid flows in direction 18 through a passageway 21 in line 14. Passageway 21 permits light (shown as dotted lines in FIGS. 1 and 2) from laser 20 to pass through onto imaging optics 22. Imaging optics 22 projects a magnified image of the interior of passageway 21 onto planar detector 26. Member 22 can be any appropriate and known means for producing a magnified optical image, including simple or compound lenses, provided that it is capable of producing images of objects with the desired spatial resolution. The magnification is chosen in conjunction with the planar detector 26 to provide sufficient resolution to detect particulates of the order of 10 micrometers or smaller. Detector 26 is preferably a conventional planar array of light sensitive photodiodes or phototransistors, for transducing the image into corresponding electronic data. Cable 28 transmits this data to a processor, preferably a computer programmed to analyze the image, in a manner discussed further below.

Figure 2:
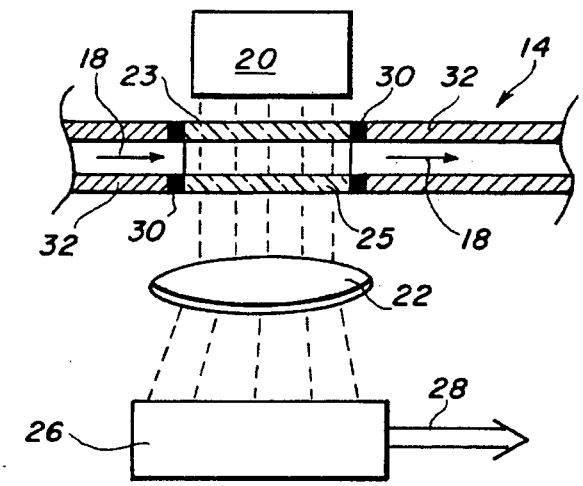
FIG. 2 is a schematic, with parts in section, illustrating one embodiment of an imaging system according to the invention.

The embodiment of FIG. 2 is similar to that of FIG. 1, in which passageway 21 is in the form of a pair of optical plates 23, 25 located between laser 20 and optics 22. Plates 23, 25 are bonded in a fluid tight manner at 30 to form a conduit for the fluid. Bonding can be done in any conventional manner, e.g. heat pressing or epoxying.

Figure 3:
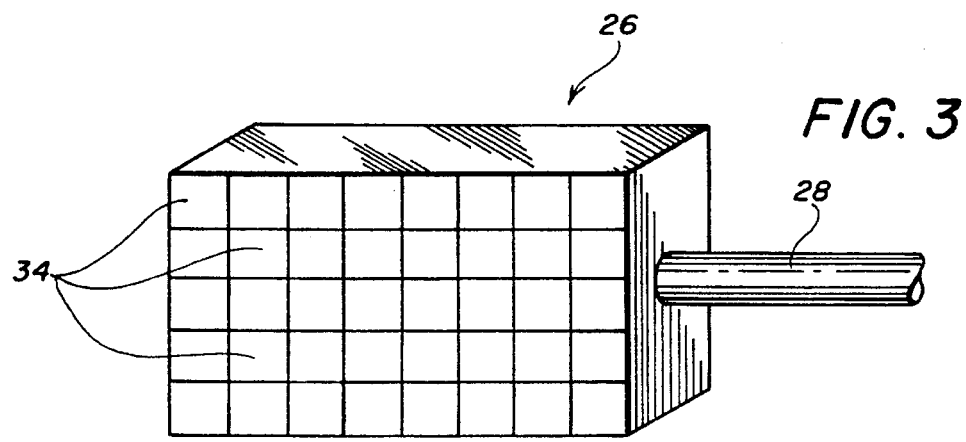
FIG. 3 is a schematic of a detector array useable with the invention.

FIG. 3 illustrates a conventional photodetector array, such as could be used for detector 26 in FIGS. 1 or 2. The array is a planar matrix of cells 34, each of which contains a light sensitive device, such as a photodiode or phototransistor. Presence of light triggers current output by the devices of pixels 34 in proportion to light intensity. Projection of an image onto pixels 34 thus causes the image to be converted to a plurality of current magnitudes, which when integrated provide a pixel-wise representation of the image in the form of charge magnitudes. In this manner, the image is converted to electronic data, which can be read out via data line 28 for processing.

The duration of the pulses is chosen in accordance with the flow rate of fluid in line 14, so as to image as much of the fluid as possible, and thus improve the quality of statistical sampling of particle size and shape. Thus if laser 20 illuminates all of passageway 21, the desired pulse repetition period is the time necessary for a complete fluid volume in the passageway to clear. If the laser illuminates only a fraction of passageway 21, the preferred repetition period is reduced by that fraction, etc. The width of passageway 21 in the direction of light travel is sufficiently small so that the diffraction pattern from the interior of passageway 21 represented by light exiting passageway 21 is characterized by the system's optical near field. Passageway 21's depth is determined by the depth of field necessary to sharply image particles of interest. For objects less than 50 microns across, passageway 21 should nominally be on the order of 200 to 250 microns wide.

Laser 20 is preferably a commonplace laser diode, and is chosen to be of a frequency to which fluid in passageway 21 is effectively transparent. For synthetic based oils commonly used in aircraft (e.g. as specified by U.S. Department of Defense military lubricant specification MIL L 236997808), or human blood, a laser radiating at 850 nm would be effective and otherwise appropriate.

In operation, the embodiments of FIGS. 1 and 2 are triggered by a timing clock (not shown) which causes laser 20 to discharge a pulse of coherent light through passageway 21, which is imaged onto detector array 26. Particulates in the fluid appear as dark shapes in the image. The same pulse (appropriately delayed to permit charging of the pixels in detector 26) also triggers array 26 to transmit its electronic version of the image to a computer (not shown) for processing. Repeatedly triggering the system in this manner builds up over time statistically useful information about the particulates in the fluid, despite the very small volume of fluid present in passageway 21 at any one time.

Figure 4:
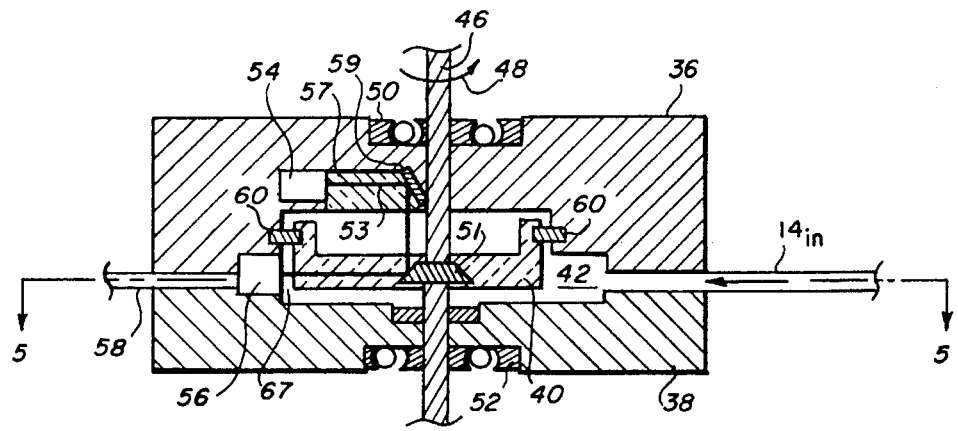
FIGS. 4–5 illustrate another embodiment of an imaging system according to the invention.
Figure 5:
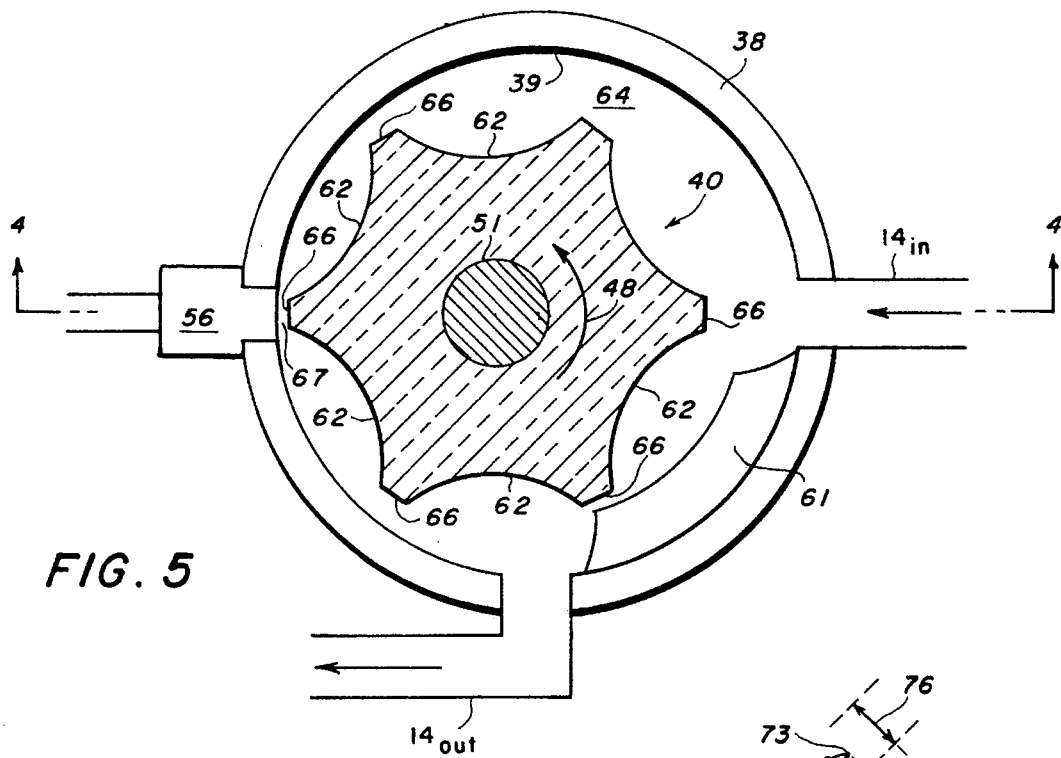

FIGS. 4–5 illustrate an alternative scheme for imaging the fluid. Two members 36, 38 form a casing which defines therebetween a space 42 in fluid contact with input portion $14_{in}$ and output portion $14_{out}$ of line 14. Space 42 is separated from the remainder of the interior of casing 36, 38 by seals 60. Penetrating casing 36, 38 is shaft 46 of rotary member 40. Member 40 is made of material which is transparent to output of laser 54, and has a planar portion which is perpendicular to shaft 46 (best seen in FIG. 5) which contains a conical reflector 51 disposed symmetrically about shaft 46. Rotor 46 is mounted via bearings 50, 52 in casing 36, 38 for rotation (as indicate at 48) about the central axis of shaft 48. Penetrating casing member 36 is a laser (or optical transmission line for delivery of laser output) 54. Laser 54 is connected optically via optical glass 57 to mirror 59, which are mounted within member 36 to direct light 53 emitted from 54 to mirror 51 and thence to a combined optics package and detector 56, which performs the same function as optics 22 and detector 26 in the embodiments of FIGS. 1–3 (and which for simplicity will be referred to as "detector package" 56). Data line 58 penetrates casing 36, 38 to relay data from detector package 56.

As best seen in FIG. 5, the planar portion of member 40 has a plurality of scallops 62 circumferentially disposed about its periphery which define therebetween a corresponding of circumferentially disposed protrusions 66. The axis of rotation of portion 46 is asymmetrically located within opening 42, so that inner wall 39 of member 38 is increasingly closer to protrusions 56 as one proceeds from inlet $14_{in}$ to detector package 56, and then becomes increasingly large up to outlet $14_{out}$, and then smaller again due to ridge 61 extending radially outwards from casing member 38.

In operation, tapped fluid enters opening 42 via line $14_{in}$ which exposes it to rotary member 40 which is being rotated by an external motor (not shown). (The rotation is counter-clockwise from the viewpoint of FIG. 5.) Scallops 62 scoop the fluid and carry it with rotary member 40 towards detector package 56. Because inner wall 39 of member 38 becomes increasingly near scallops 62 as member 40 moves towards detector package 56, the fluid becomes compacted, and sheared by protrusions 66. In this manner, the fluid is forced into a thin film 67 between detector package 56 and the protrusions 66 as they pass by. Pulsed light from laser 54 travels via mirrors 51, 59, and the optical glass constituting members 57 and 40, to gap 67 and thence to detector package 56, and via data output 58, to a computer (not shown) for processing. In this manner, gap 67 is imaged in the same manner as passageway 21 of FIGS. 1–2. After passing detector 56, fluid in scallops 62 move towards output $14_{out}$ where protrusions 66 cooperate with ridge 61 to force the fluid out of casing 36, 38.

Figure 7:
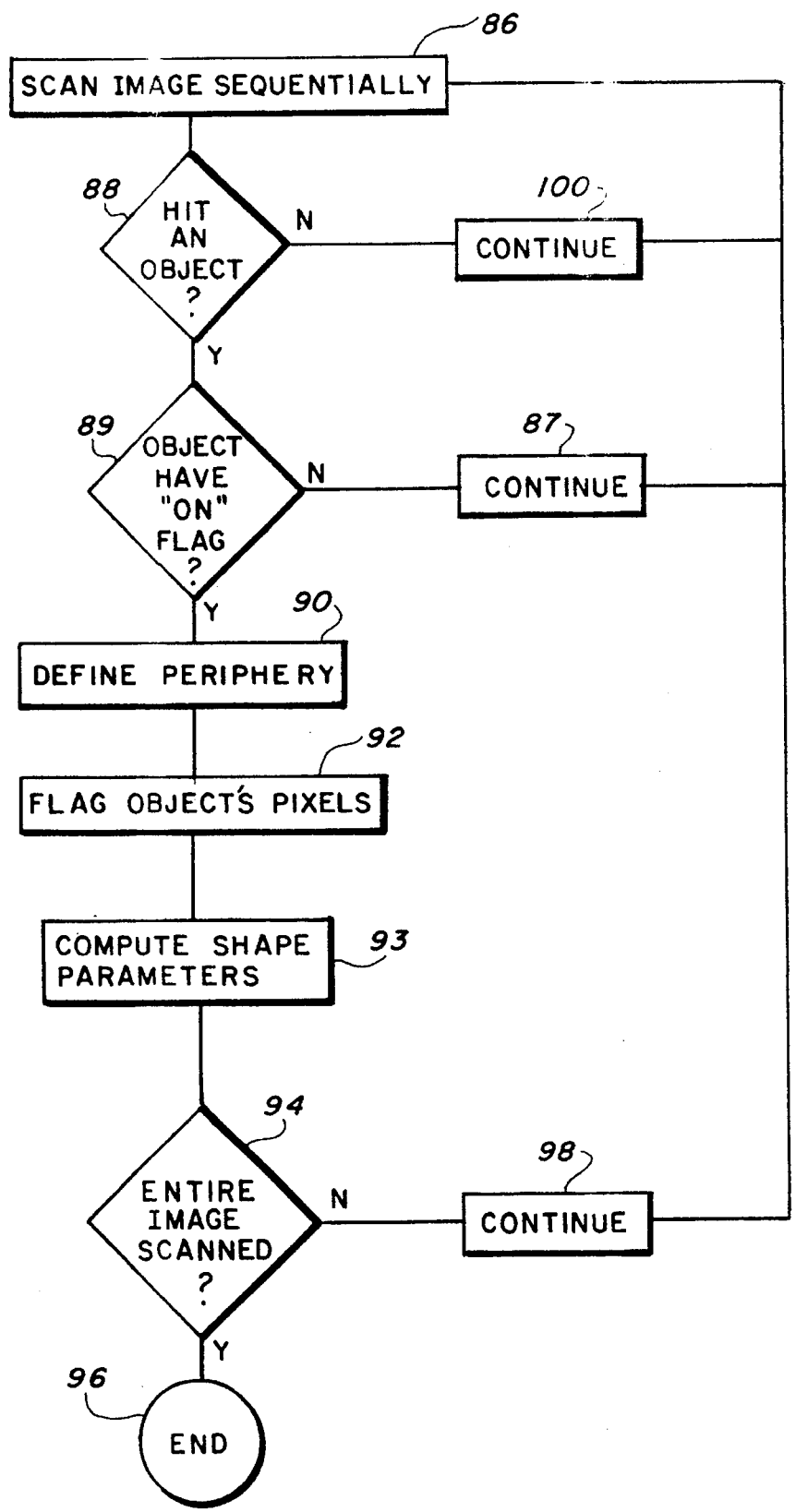
FIG. 7 is a flow chart illustrating a way of identifying particulate shape.

FIG. 7 shows a method of identifying the sizes and shapes of particulates imaged in gap 67 or passageway 21. Taking the individual pixel data output from detectors 28 or 56, and preferably using a dedicated computer, one scans the image (86) sequentially pixel by pixel (e.g. row by row) until one locates a pixel (88) having a preselectedly low signal, indicating that an object shadowed light from the pixel during imaging. One then determines if this pixel has a "flag" on it (89) indicating that the pixel belongs to a group of pixels which constitute the image of an object which has already been encountered in the scan (89). If no flag, one then uses conventional chain code to identify the pixels constituting the periphery of the object (90), and flag those pixels in computer memory so that subsequent processing will not re-do that object (92). One then uses the chain coded periphery of the object to compute whatever parameters one wishes to use to characterize object shape (aspect ratio, longest linear dimension, etc.) (93). One continues this process (87, 94, 98, 100, 102) until one has scanned the entire image, outputs data gotten about objects in the image (preferably updates a histogram of particulate shapes) and ends processing pending receipt of additional image data. This method is especially simple to program, which eases coding, and lends itself well to parallel implementation (e.g. using several processors in parallel to simultaneously process different sectors of an image).

Figure 6:
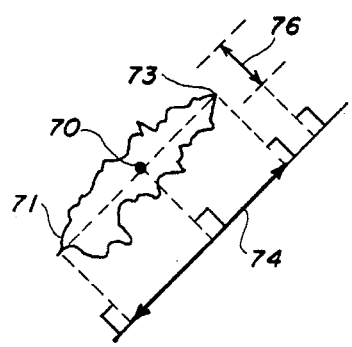
FIG. 6 shows two a common particulate shape, and illustrates ways to characterize its shape according to the invention.

Having characterized particulate shape in the form of chain code, one can use the characterization to calculate any of numerous parameters associated with shape, so as to classify the object. FIG. 6 shows a particulate such as one might find in used engine oil, jagged with a long dimension 74, and short dimension 76. Because its shape, i.e. periphery, would be recorded in chain code, by simple analytical geometry one can readily identify axes 74, 76, and their respective lengths. Their ratio is the object's aspect ratio, a measure of its thinness. Both aspect ratio and longest axis provide important information about, e.g., engine condition: long, thin, particulates can indicate excessive cutting wear; longest axis can indicate how far engine wear has progressed (with sheading of larger particulates expected nearer to engine failure).

The invention has been described in what is considered to be the most practical and preferred embodiments. It is recognized, however, that obvious modifications to these embodiments may occur to those with skill in this art. Accordingly, the scope of the invention is to be discerned from reference to the appended claims, wherein:

We claim:

1. A particle classifier comprising:

means for diverting fluid from a flow line into a passageway;

a source of coherent light;

optical means, responsive to coherent light from said source, for periodically imaging said fluid in said passageway onto an optical detector, said detector being effective to transduce said image into electronic pixel information;

wherein the width of said passageway in the direction transverse to said passageway is selected to be of a size which causes the diffraction pattern formed of the interior of said passageway by said light passing through said passageway to be of the near field of said interior;

said classifier further comprising an analysis means for classifying, responsive to said electronic pixel information, the distribution of sizes or shapes of objects in said image.

2. A method of particle classification comprising:

diverting fluid from a flow line into a passageway;

providing a source of coherent light;

responsive to coherent light from said source, periodically imaging said fluid in said passageway onto an optical detector, said detector being effective to transduce said image into electronic pixel information;

selecting the width of said passageway in the direction transverse to said passageway to be of a size which causes the diffraction pattern formed of the interior of said passageway by said light passing through said passageway to be of the near field of said interior;

classifying, responsive to said electronic pixel information, the distribution of sizes or shapes of objects in said image.

3. An apparatus comprising:

a casing having a fluid inlet and a fluid outlet;

a rotary member disposed for rotation in a plane in said casing about an axis transverse to said plane;

means for rotating said rotary member in said plane about said axis;

wherein said rotary member has a plurality of scallops disposed about the circumference of said rotary member in said plane to form a corresponding plurality of concave depressions for receiving fluid in said casing, and to form between said scallops a plurality of protrusions;

wherein said axis is disposed asymmetrically within said casing effective to cause said protrusions to be alternatingly nearer to and distant from said casing as said rotary member rotates in said plane effective to create increasingly smaller distances between said protrusions and said casing about the circumference of said rotary member disposed in said plane between said inlet and said outlet in the direction of said rotation of said rotary member;

wherein said casing comprises a source of light disposed effective to radiate coherent light towards said rotary member in said plane; and wherein the distance between said protrusions and said source of light constitutes an imaging gap, said imaging gap being selected to be of a size to cause the diffraction pattern formed by said light passing through said imaging gap to be of said gap's optical near field.

4. The apparatus of claim 3, wherein:

said light passing through said imaging gap constitutes an optical image of said gap, said apparatus further comprising:

an optical detector disposed to receive said image; and means, disposed between said gap and said optical detector, for magnifying said image onto said detector.

\* \* \* \* \*

UNITED STATES PATENT AND TRADEMARK OFFICE
CERTIFICATE OF CORRECTION

PATENT NO. : 5,572,320
DATED : November 5, 1996
INVENTOR(S) : Reintjes et al.

Page 1 of 1

It is certified that error appears in the above-identified patent and that said Letters Patent is hereby corrected as shown below:

<u>Title page,</u>
Item [75], should read:
-- Inventors: John F. Reintjes, Alexandria, Virginia
Paul L. Howard, Westchester, Pennsylvania
Michael D. Duncan, Cheverly, Maryland
Rita Mahon, Silver Spring, Maryland
Lawrence L. Tankersley, Annapolis, Maryland
Abraham Schultz, Alexandria, Virginia
Victor Chen, Vienna, Virginia
Jefferson Willey, Columbia, Maryland --

Signed and Sealed this

Eleventh Day of May, 2004

JON W. DUDAS
*Acting Director of the United States Patent and Trademark Office*